United States Patent [19]

Naughton et al.

[11] Patent Number: 4,721,096
[45] Date of Patent: Jan. 26, 1988

[54] PROCESS FOR REPLICATING BONE MARROW IN VITRO AND USING THE SAME

[75] Inventors: Brian A. Naughton; Gail K. Naughton, both of Yorktown Heights, N.Y.

[73] Assignee: Marrow-Tech Incorporated, Albany, N.Y.

[21] Appl. No.: 36,154

[22] Filed: Apr. 3, 1987

Related U.S. Application Data

[63] Continuation of Ser. No. 853,569, Apr. 18, 1986, abandoned.

[51] Int. Cl.$^4$ .......................... A61B 19/00; C12N 5/02
[52] U.S. Cl. .............................. 128/1 R; 435/240.21; 435/240.23; 435/240.3
[58] Field of Search ................ 128/1 R; 435/240, 241

[56] References Cited

U.S. PATENT DOCUMENTS

| | | | |
|---|---|---|---|
| 4,107,937 | 8/1978 | Chmiel | 62/64 |
| 4,117,881 | 10/1978 | Williams et al. | 165/2 |
| 4,135,975 | 1/1979 | Lichtman et al. | 195/1.8 |
| 4,342,828 | 8/1982 | Takaku et al. | 435/41 |
| 4,402,934 | 9/1983 | Teodorescu et al. | 435/241 |
| 4,436,816 | 3/1984 | Dinka | 435/240 |
| 4,481,946 | 11/1984 | Altshuler et al. | 604/4 |
| 4,486,188 | 12/1984 | Altshuler et al. | 604/4 |
| 4,508,819 | 4/1985 | Rose | 435/240 |

FOREIGN PATENT DOCUMENTS

0163543 12/1985 European Pat. Off. .

OTHER PUBLICATIONS

T. M. Dexter et al., "Long-Term Marrow Culture: An Overview of Techniques and Experience", in *Long-Term Bone Marrow Culture*, pp. 57–96, edited by D. Wright et al., Alan R. Liss, Inc., New York, (1984).

F. Van De Ouweland et al., "Enrichment and Cryopreservation of Bone Marrow Progenitor Cells for Autologous Reinfusion", *Cryobiology*, vol. 19, pp. 292–298, (1982).

N. C. Gorin et al., "Long-Term Preservation of Bone Marrow and Stem Cell Pool in Dogs", *Blood*, vol. 51, No. 2, (Feb. 1978).

J. Chang et al., "Reconstitution of Haemopoietic System With Autologous Marrow Taken During Relapse of Acute Leukaemia and Grown in Long-Term Culture," *The Lancet*, pp. 294–295 (Feb. 8, 1986).

*Primary Examiner*—John D. Yasko
*Attorney, Agent, or Firm*—Pennie & Edmonds

[57] ABSTRACT

According to the present invention there is provided a process for treating a person whose bone marrow has been destroyed or lost its functional ability. The process includes the steps of obtaining bone marrow from a donor, cryopreserving the marrow, replicating the bone marrow cells in vitro, and then infusing the replicated bone marrow cells into a person whose bone marrow has been destroyed or functionally compromised by disease or the treatment of disease. The person receiving the replicated bone marrow infusion may be the donor or another person. There is also disclosed a process for replicating bone marrow in vitro.

12 Claims, No Drawings

PROCESS FOR REPLICATING BONE MARROW IN VITRO AND USING THE SAME

This is a continuation of application Ser. No. 853,569 filed Apr. 18, 1986, now abandoned.

Processes for transplanting bone marrow are known. Generally, bone marrow transplants are performed on patients who suffer from a disease, such as cancer, which destroys healthy bone marrow cells or depresses their functional ability. In addition, treatments such as chemotherapy or radiation therapy adversely affect the bone marrow even in cases where the bone marrow has not been directly affected by the disease being treated. Known methods of bone marrow transplantation suffer from a number of disadvantages. One major cause of bone marrow transplant rejection is the graft versus host reaction which occurs when bone marrow removed from one person is transplanted into another person. Another major cause of bone marrow transplant failure is vasoocclusive disease resulting from the formation of marrow emboli. Procedures for the removal and storage of a person's marrow prior to combined chemotherapy and radiation and reinfusion of that marrow currently exist (i.e., autologous transplant). However, the patient often suffers from recurrence of the disease even if engraftment occurs since the marrow was already diseased when first removed.

Therefore, it is an object of the present invention to provide a process for treating diseases that destroy healthy bone marrow cells or depress their functional or replicative ability which process does not suffer from the known disadvantages of current bone marrow transplantation techniques.

Another object of the present invention is to provide a process for treating diseases by bone marrow transplantation which process does not produce a graft versus host reaction.

A further object of the present inveniton is to provide a process for treating diseases by bone marrow transplantation which does not cause the formation of marrow emboli.

Yet another object of the present invention is to provide a means for treating diseases or conditions that destroy healthy bone marrow cells by aspirating bone marrow from a patient, replicating the bone marrow cells in vitro and then reinfusing the replicated marrow cells into the patient.

A still further object of the present invention is to provide a process for increasing the functional ability of a bone marrow which has been adversely affected by chemotherapy and/or radiation therapy.

Still another object of the present invention is to provide a process for the treatment of hematalogical malignancies and other neoplasias which metastasize to the bone marrow.

Additional objects and advantages of the present invention will be apparent to those skilled in the art by reference to the following detailed description.

SUMMARY OF THE INVENTION

According to the present invention, there is provided a process for treating diseases or conditions which have destroyed healthy bone marrow cells or have depressed their functional ability. The process of the present invention is especially effective in the treatment of hematological malignancies and other neoplasias which metastasize to the bone marrow. The process of the present invention comprises the steps of: aspirating a small amount of bone marrow from a healthy patient; replicating the bone marrow cells in vitro to expand the bone marrow cells to volumes sufficient for autologous reinfusion in amounts greater than originally removed from the patient; and then reinfusing the bone marrow cells into the patient. According to one embodiment of the present invention, the bone marrow cells are cryopreserved or frozen immediately after aspiration from the patient and are subsequently thawed and replicated. According to another embodiment of the present invention, an allogeneic bone marrow transplant is performed by aspirating bone marrow from one person, replicating the marrow cells in vitro, and then infusing the replicated marrow cells into another person.

DETAILED DESCRIPTION OF THE INVENTION

The present invention is directed to a process for treating diseases or conditions which destroy healthy bone marrow cells or depress their functional ability. The process is especially effective in the treatment of hematalogical malignancies and other neoplasias which metastasize to the bone marrow. The process of this invention is also effective in treating patients whose bone marrow has been adversely affected by chemotherapy and/or radiation therapy necessitated by a disease which does not directly affect the bone marrow. The process of the present invention further provides a means for removing and preserving bone marrow cells from a healthy patient and then replicating and reinfusing the bone marrow cells should the patient develop an illness which either destroys the bone marrow directly or whose treatment adversely affects the marrow.

In accordance with the process of the present invention, a small amount of bone marrow is aspirated from the iliac crest of a donor. Methods of aspirating bone marrow from a donor are well known in the art. Examples of apparatus and processes for aspirating bone marrow from a donor can be found in U.S. Pat. No. 4,481,946 and U.S. Pat. No. 4,486,188.

The bone marrow removed from the donor is then replicated or preserved for future replication. If the bone marrow is to be preserved, the bone marrow can be incrementally frozen using computerized cryotechnological equipment. The cellular viability of bone marrow cells preserved by current methods of cryopreservation exceeds 90%. Examples of systems for freezing bone marrow and biological substances in accordance with a precalculated temperature-time curve are disclosed in U.S. Pat. No. 4,107,937 and U.S. Pat. No. 4,117,881. Preferably, the bone marrow cells are stored in liquid nitrogen at a temperature, e.g. $-196°$ C., at which all activity of the marrow cells, including cell replication, has ceased.

The process of the present invention further comprises the step of replicating the bone marrow cells in vitro. The bone marrow cells, either obtained directly from the donor or retrieved from cryopreservative storage, are first separated from their reticulum. The bone marrow cells are then grown in co-cultures with stromal components of normal marrow including fibroblasts, macrophages, reticular cells, and adipocytes or with factors derived from culture media or these cells as well as substances produced in vitro by hepatic (liver) and splenic (spleen) macrophages. Although marrow cells are capable of limited growth when cultured alone, long term growth of these cultures is possible only if stromal cells or their secretory products are added. The present invention seeks to maximize the proliferation of a multipotential hematopoietic stem cell which has the capability of repopulating bone marrow which has been destroyed by intrinsically or environmentally-mediated disease or by the treatment of such disease with chemotherapy and/or radiation. Stem cells which have marrow repopulating activity (MRA) have been shown to persist and replicate in long term bone marrow cultures.

According to a preferred embodiment of the present invention, hematopoietic stem cells, which are marrow cells having the capability of repopulating bone marrow which has been destroyed, are plated onto dishes containing a reticular fiber network. The reticular fiber network is pre-established by subsetting fibroblasts as described hereinafter. The hematopoietic stem cells are grown in a modified Fischers' medium enriched with 20-25% fetal bovine serum or 20-25% human serum. Secretory products of the different populations of normal marrow stromal cells and extramedullary macrophages, the preparation of which are described below, as well as known inducers of cell division are added to the culture to promote the growth of multipotential stem cells, specifically those with MRA.

Medullary macrophages, fibroblasts, adipocytes, and reticular cells can be isolated from the "buffy coat" of a marrow cell suspension after centrifugation of 2.5 ml of donor marrow. After removal of the buffy coat layer, the remaining marrow (containing the hematopoietic cells) is incrementally cryopreserved.

The stromal cells are washed with Fischers' medium (GIBCO) supplemented with 20-25% fetal bovine serum or 20-25% human serum. The fibroblastic elements of this suspension are subsetted using methods described hereinafter. Cells producing reticular fibers and cells capable of synthesizing collagen are plated in a volume containing $2 \times 10^5$ cells onto a sterile nylon sieve which is suspended in a plastic culture dish. The non-adherent cell layer is removed by washing with the culture medium every 6 days. When sufficient stroma is deposited by these cells (approximately 3-4 weeks), the remaining aliquot of marrow sample will be thawed, suspended in Fischers' medium enhanced with 20-25% fetal bovine serum or human serum, and plated onto the stromal template in volumes containing $2-4 \times 10^6$ cells. Cultures are grown at 33° C. in 5-6% $CO_2$ in ambient air. Non-adherent cells are removed every 5 days, washed in culture medium, and centrifuged. The pellets containing these non-adherent cells will be incrementally cryopreserved for possible future use. This step is performed because it has been shown that some hematopoietic stem cells are found amongst the non-adherent cells.

Macrophages, reticular cells, adipocytes, and fibroblasts may also be grown at 33° C. in separate culture dishes at cell concentrations of $6-8 \times 10^6$/ml in Fischers' medium as described above. The secretory activities of these cells may be modulated via treatment of the cultures with prostaglandins E and A, interleukins 2 and 3, and by varying the $CO_2/O_2$ ratio in $N_2$. Products of these cells may be used in stimulating the replication of the hematopoietic stem cells and will be cryopreserved for possible future use.

Extramedullary macrophages, namely the Kupffer cells of the liver and the splenic macrophages, are separated from their organ stroma by the following methods. Suspensions of littoral cells in the liver and spleen will be derived from a pronase digestion of these organs. Briefly, tissue specimens will be incubated for 1 hr at 37° C. in pronase solution (0.2% pronase (Calbiochem) and Geys' Balanced Salt Solution (BSS)) while being gently agitated. The pH of the solution is maintained at 7.3-7.5 with 1N NaOH. Deoxyribonuclease (0.5 mg) (Calbiochem) is added at 30 min intervals during the above procedure and the resultant cell suspension is filtered and centrifuged at $350 \times G$ for 10 min. The pellet is resuspended in Geys' BSS and the littoral cells (macrophages and endothelial cells) are separated from the cellular debris and mature blood cells using a Percoll (Pharmacia) gradient. The resultant cell fraction is washing $3 \times 3$ min with a modified Dulbecco's medium enriched with 10% fetal bovine serum and plated onto plastic culture dishes at a volume containing $3-4 \times 10^6$ cells. After incubation for 1 day, the non-adherent cells are removed by washing with culture medium and the adherent cells are maintained at 33° C. in a gas mixture consisting of 5-6% $CO_2$ in room air. The growth and/or secretory activity of these cells will be modulated by: 1. varying the $CO_2/O_2$ ratio, 2. adding prostaglandins $E_2$, $E_1$, or A to the medium, 3. supplementing the medium with interleukin 2 or interleukin 3, and 4. adding latex beads to the cultures. Macrophages will release their stored secretory products when they phagocytize these objects. Macrophage secretory products which are released into the culture medium will be cryopreserved for use in supplementing the bone marrow culture medium. Macrophages are cells with a high degree of secretory potential. They have been shown to store and/or synthesize erythropoietin, colony stimulating factor, and several prostaglandins. These cells and their secretions are a fundamental part of the microenvironment necessary for hematopoietic stem cells to develop.

Fibroblasts are grown in culture using Fischer's medium supplemented with 20% fetal bovine serum to which 2 $\mu$g/ml gentamycin, penicillin, streptomycin, and fungizone have been added. Subsets of these fibroblasts may be isolated according to their ability to synthesize specific components of the extracellular matrix. Fibroblasts derived from the "buffy coat" of a bone marrow suspension of donor cells (or cells taken from cadaver liver with similar HLA characteristics) are plated onto microtiter wells (1 mm$^2$) and grown to confluency. Fibroblasts are lifted from culture wells by repeated washings (4-5x) with Hank's BSS without $Ca^{++}$ or $Mg^{++}$. The cultures are treated with monoclonal antibodies directed against collagen types I-V, elastin, tropoelastin and fibronectin. The cultures are then treated with fresh guinea pig complement. After complement mediated lysis of sensitized fibroblasts, only those cells capable of producing reticular fibers will remain. Clonal isolation of other types of fibroblasts can be performed in a similar manner. Mixtures of fibroblasts with the ability to make reticular fibers and collagen fibers will be plated onto a sterile nylon sieve which is suspended in the plastic culture dish containing enhanced Fischer's medium. Non-adherent cells are removed by washing with culture medium at 72 hour intervals. Deposition of stroma by these fibroblasts on the nylon template will be verified with an inverted phase contrast microscope. Sufficient matrix will be secreted by the original inoculum of $5 \times 10^6$ cells to support hematopoiesis in approximately 3-4 weeks.

Reticular fibers are an important component of the extracellular matrix of any hematopoietic tissue. In the body, high concentrations of this glycoprotein fiber are found in organs such as the bone marrow, liver, spleen and peripheral lymphatic organs. The use of reticular fibers as matrix material augments the growth of hematopoietic stem cells. The secretory products of the other fibroblasts are also preserved for use in the stem cell culture system. Certain products of the cells, such as the glycosaminoglycans, have proven to be important to the continued proliferation of bone marrow cells in culture.

Marrow cells grown in accordance with the replication process of the present invention can be re-infused into the donor at such time as his own marrow becomes diseased or is adversely affected by medical treatment, such as chemotherapy or radiation, or environmental factors. Since this is essentially an autologous transplant of an individual's own tissue, there is little chance of rejection of the bone marrow and no possibility of viral contamination from another person.

The cultured stem cells grown in accordance with the method of the present invention may be used in bone marrow transplants between different individuals. For utilization in transplants between different individuals, it may be necessary to remove mature T lymphocytes from the initial marrow sample by lectin agglutination and E-rosette depletion prior to replication of the stem cells. This procedure has diminished the graft vs. host complications currently associated with allogeneic bone marrow transplantation. This additional step may, however, prove to be unnecessary. Marrow cells, when grown in long term culture, display a significantly lower immunogenicity and may, therefore, not elicit the graft vs. host reaction in any case.

After the marrow cells have been replicated in culture as described above, the marrow cells are intravenously infused into a person in need of a bone marrow transplant. If the marrow had been cryopreserved, the marrow will be thawed prior to replication. Seeding of the multipotential stem cells of the replicated marrow in either a medullary or extramedullary site will restore hematopoiesis in a person whose marrow has been destroyed by disease itself or by the treatment of disease.

The process of the present invention has several advantages to a patient in need of a bone marrow transplant. If the patient is receiving his or her own cells, this is an autologous transplant with little likelihood of rejection. This eliminates a major cause of bone marrow transplant rejection, that is, the graft vs. host reaction. Further, when grown in culture, hematopoietic stem cells are relatively non-adherent. This non-adherence of the hematopoietic stem cells may diminish the risk of vasoocclusive disease resulting from marrow embolus. In addition, the process of the present invention allows more aggressive treatment of neoplastic disorders with chemotherapeutic agents and radiation. Presently, the extent of these treatments is often limited by bone marrow toxicity.

Although the invention is described in detail with reference to specific embodiments thereof, it will be understood that variations can be made without departing from the scope of the invention as described above and as claimed below.

What is claimed is:

1. A process for treating a person whose bone marrow has been destroyed or lost its functional ability, said process comprising the steps of:
   I. obtaining a bone marrow sample from a donor; and then
   II. replicating the bone marrow sample in vitro to produce a replicated bone marrow containing hematopoietic stem cells having marrow repopulating activity; and then
   III. infusing the replicated bone marrow containing hematopoietic stem cells into the person to restore hematopoiesis in the person.

2. The process of claim 1 further comprising the step of cryopreserving the bone marrow sample prior to replicating the bone marrow sample.

3. The process of claim 1 wherein the bone marrow sample is obtained by aspirating a bone marrow sample from the iliac crest of the donor.

4. The process of claim 1 wherein the donor of Step I and the person of Step III are the same person.

5. The process of claim 1 wherein the donor of Step I and the person of Step III are different persons.

6. The process of claim 1 wherein the bone marrow sample is replicated in vitro by growing bone marrow cells of the bone marrow sample, including hematopoietic stem cells, in a culture containing secretory products of normal marrow stromal cells and secretory products of extramedullary macrophages.

7. The process of claim 6 further comprising the step of plating the bone marrow cells on a dish containing a reticular fiber network prior to growing the bone marrow cells in the culture.

8. The process of claim 7 further comprising the step of subsetting fibroblasts to produce the reticular fiber network.

9. The process of claim 6 further comprising the step of producing the secretory products of extramedullary macrophages by growing extramedullary macrophage cells in the presence of prostaglandins $E_2$, $E_1$ and A.

10. The process of claim 9 wherein the extramedullary macrophages are hepatic and splenic macrophages.

11. The process of claim 9 wherein the extramedullary macrophage cells are grown in the presence of latex beads.

12. The process of claim 6 further comprising the step of producing the secretory products of marrow stromal cells by growing marrow stromal cells in the presence of prostaglandins and interleukins.

* * * * *